US011725046B2

(12) United States Patent
Liao et al.

(10) Patent No.: US 11,725,046 B2
(45) Date of Patent: Aug. 15, 2023

(54) HUMAN NEUTRALIZING ANTI-TETANUS TOXIN MONOCLONAL ANTIBODY AND ITS APPLICATIONS

(71) Applicant: ZHUHAI TRINOMAB BIOTECHNOLOGY CO., LTD., Guangdong (CN)

(72) Inventors: Huaxin Liao, Guangdong (CN); Yueming Wang, Guangdong (CN); Xiaohui Yuan, Guangdong (CN); Weihong Zheng, Guangdong (CN)

( * ) Notice: Subject to any disclaimer, the term of this patent is extended or adjusted under 35 U.S.C. 154(b) by 138 days.

(21) Appl. No.: 16/958,213

(22) PCT Filed: Dec. 28, 2018

(86) PCT No.: PCT/CN2018/124958
§ 371 (c)(1),
(2) Date: Jun. 26, 2020

(87) PCT Pub. No.: WO2019/129214
PCT Pub. Date: Jul. 4, 2019

(65) Prior Publication Data
US 2021/0002356 A1    Jan. 7, 2021

(30) Foreign Application Priority Data

Dec. 29, 2017  (CN) .......................... 201711482969.7
Dec. 29, 2017  (CN) .......................... 201711486693.X
Dec. 29, 2017  (CN) .......................... 201711486732.6
May 4, 2018    (CN) .......................... 201810420730.5

(51) Int. Cl.
*C07K 16/12*      (2006.01)
*G01N 33/569*     (2006.01)
*G01N 33/577*     (2006.01)

(52) U.S. Cl.
CPC .... *C07K 16/1282* (2013.01); *G01N 33/56911* (2013.01); *G01N 33/577* (2013.01); *C07K 2317/21* (2013.01); *C07K 2317/76* (2013.01); *C07K 2317/92* (2013.01); *G01N 2333/33* (2013.01)

(58) Field of Classification Search
CPC ............ C07K 16/1282; C07K 2317/21; C07K 2317/76; C07K 2317/92; C07K 2317/56; C07K 2317/565; G01N 33/56911; G01N 33/577; G01N 2333/33
See application file for complete search history.

(56) References Cited

U.S. PATENT DOCUMENTS 6,657,103 B1 * 12/2003 Kucherlapati ....... C07K 16/244
                                                  435/320.1
2004/0253242 A1 * 12/2004 Bowdish ................ C07K 16/46
                                                  424/145.1

OTHER PUBLICATIONS

Padlan et al. Proc Natl Acad Sci USA, 86:5938-5942. (Year: 1989).*
Rudikoff et al. Proc Natl Acad Sci USA, 79(6):1979-1983. (Year: 1982).*
Paul WE, editor, Fundamental Immunology, Third Edition, pp. 292-295, under the heading "Fv Structure and Diversity in Three Dimensions". (Year: 1993).*

* cited by examiner

*Primary Examiner* — Kimberly Ballard
(74) *Attorney, Agent, or Firm* — Yuanyue Ma; Law Office of Yuanyue Mu PLLC

(57) ABSTRACT

The invention describes fully native human neutralizing monoclonal antibodies against tetanus toxin. The invention developed fully native human neutralizing monoclonal antibodies against tetanus toxin through a systematic high through-put platform that is specialized for identifying and developing human native antibody. The neutralizing monoclonal antibodies described in the invention can be used in the prevention, treatment and detection of *Clostridium tetani* infection. The fully human neutralizing monoclonal antibodies developed in the invention have a high affinity toward tetanus toxin, as well as possessing high neutralizing activities against the toxin, safe of use with high disease prevention effectiveness, free of exogenous virus contamination, and are widely applicable to various human groups with strong industrial applications.

15 Claims, 5 Drawing Sheets
Specification includes a Sequence Listing.

```
                        SEQUENCE LISTING

<160> NUMBER OF SEQ ID NOS: 34

<210> SEQ ID NO 1
<211> LENGTH: 8
<212> TYPE: PRT
<213> ORGANISM: Homo sapiens

<400> SEQUENCE: 1

Gly Gly Ser Ile Ser Ser Tyr Tyr
1               5

<210> SEQ ID NO 2
<211> LENGTH: 7
<212> TYPE: PRT
<213> ORGANISM: Homo sapiens

<400> SEQUENCE: 2

Val His Tyr Ser Gly Ser Thr
1               5

<210> SEQ ID NO 3
<211> LENGTH: 12
<212> TYPE: PRT
<213> ORGANISM: Homo sapiens

<400> SEQUENCE: 3

Ala Arg Asp Lys Tyr Gln Thr Asp Val Ser Asp Ile
1               5                   10

<210> SEQ ID NO 4
<211> LENGTH: 7
<212> TYPE: PRT
<213> ORGANISM: Homo sapiens

<400> SEQUENCE: 4

Gln Ser Ile Thr Ser Ser Phe
1               5

<210> SEQ ID NO 5
<211> LENGTH: 4
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Gly Ala Ser Xaa
1

<210> SEQ ID NO 6
<211> LENGTH: 8
<212> TYPE: PRT
```

```
<213> ORGANISM: Homo sapiens

<400> SEQUENCE: 6

Gln Gln Tyr Asp Thr Ser Arg Thr
1               5

<210> SEQ ID NO 7
<211> LENGTH: 118
<212> TYPE: PRT
<213> ORGANISM: Homo sapiens

<400> SEQUENCE: 7

Gln Val Gln Leu Gln Glu Ser Gly Pro Gly Leu Val Lys Pro Ser Glu
1               5                   10                  15

Thr Leu Ser Leu Arg Cys Thr Val Ser Gly Gly Ser Ile Ser Ser Tyr
                20                  25                  30

Tyr Trp Ser Trp Phe Arg Gln Pro Pro Gly Lys Gly Leu Glu Trp Ile
            35                  40                  45

Gly Tyr Val His Tyr Ser Gly Ser Thr Asn Tyr Asn Pro Ser Leu Lys
        50                  55                  60

Ser Arg Phe Thr Leu Ser Val Asp Thr Ser Lys Ser Gln Phe Ser Leu
65                  70                  75                  80

Arg Leu Arg Ser Val Thr Ala Ala Asp Thr Ala Ile Tyr Tyr Cys Ala
                85                  90                  95

Arg Asp Lys Tyr Gln Thr Asp Val Ser Asp Ile Trp Gly Gln Gly Thr
            100                 105                 110

Val Val Thr Val Ser Ser
        115

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Ser Ser
                20                  25                  30

Phe Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Ile Leu Thr Ile Ser Arg Leu Glu
65                  70                  75                  80

Pro Glu Asp Phe Ala Val Tyr Tyr Cys Gln Gln Tyr Asp Thr Ser Arg
                85                  90                  95

Thr Phe Gly Gln Gly Thr Thr Val Glu Ile Lys
            100                 105

<210> SEQ ID NO 9
<211> LENGTH: 8
<212> TYPE: PRT
<213> ORGANISM: Homo sapiens

<400> SEQUENCE: 9

Gly Tyr Thr Phe Thr Asn Tyr Trp
1               5
```

```
<210> SEQ ID NO 10
<211> LENGTH: 8
<212> TYPE: PRT
<213> ORGANISM: Homo sapiens

<400> SEQUENCE: 10

Val Tyr Pro Gly Asp Ser Asp Thr
1               5

<210> SEQ ID NO 11
<211> LENGTH: 18
<212> TYPE: PRT
<213> ORGANISM: Homo sapiens

<400> SEQUENCE: 11

Ala Thr Gln Gln Ser Asn Pro Tyr Asp Ser Gly Ser Tyr Trp Tyr Phe
1               5                   10                  15

Asp Ser

<210> SEQ ID NO 12
<211> LENGTH: 89
<212> TYPE: PRT
<213> ORGANISM: Homo sapiens

<400> SEQUENCE: 12

Gly Tyr Thr Phe Thr Asn Tyr Trp Ile Gly Trp Val Arg Gln Met Pro
1               5                   10                  15

Gly Lys Gly Leu Glu Trp Met Gly Ile Val Tyr Pro Gly Asp Ser Asp
            20                  25                  30

Thr Arg Tyr Ser Pro Ser Phe Gln Gly Gln Ile Thr Ile Ser Ala Asp
        35                  40                  45

Lys Ser Ile Ser Thr Ala Tyr Leu Gln Trp Asn Asn Leu Lys Ala Ser
    50                  55                  60

Asp Thr Gly Met Tyr Tyr Cys Ala Thr Gln Gln Ser Asn Pro Tyr Asp
65                  70                  75                  80

Ser Gly Ser Tyr Trp Tyr Phe Asp Ser
                85

<210> SEQ ID NO 13
<211> LENGTH: 6
<212> TYPE: PRT
<213> ORGANISM: Homo sapiens

<400> SEQUENCE: 13

Gln Gly Ile Arg Asn Phe
1               5

<210> SEQ ID NO 14
<211> LENGTH: 4
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Ala Ala Ser Xaa
1

<210> SEQ ID NO 15
<211> LENGTH: 9
```

```
<212> TYPE: PRT
<213> ORGANISM: Homo sapiens

<400> SEQUENCE: 15

Gln Lys Tyr Phe Ser Ala Pro Pro Asp
1               5

<210> SEQ ID NO 16
<211> LENGTH: 71
<212> TYPE: PRT
<213> ORGANISM: Homo sapiens

<400> SEQUENCE: 16

Gln Gly Ile Arg Asn Phe Leu Ala Trp Tyr Gln Gln Lys Pro Gly Lys
1               5                   10                  15

Val Pro Lys Leu Leu Ile Tyr Ala Ala Ser Thr Leu Gln Ser Gly Val
            20                  25                  30

Pro Ser Arg Phe Ser Gly Ser Gly Ser Gly Thr Asp Phe Thr Leu Thr
        35                  40                  45

Ile Ser Ser Leu Gln Pro Glu Asp Val Ala Thr Tyr Tyr Cys Gln Lys
    50                  55                  60

Tyr Phe Ser Ala Pro Pro Asp
65                  70

<210> SEQ ID NO 17
<211> LENGTH: 125
<212> TYPE: PRT
<213> ORGANISM: Homo sapiens

<400> SEQUENCE: 17

Glu Val Gln Leu Val Gln Ser Gly Ala Glu Val Lys Lys Pro Gly Glu
1               5                   10                  15

Ser Leu Arg Ile Ser Cys Gln Gly Ser Gly Tyr Thr Phe Thr Asn Tyr
            20                  25                  30

Trp Ile Gly Trp Val Arg Gln Met Pro Gly Lys Gly Leu Glu Trp Met
        35                  40                  45

Gly Ile Val Tyr Pro Gly Asp Ser Asp Thr Arg Tyr Ser Pro Ser Phe
    50                  55                  60

Gln Gly Gln Ile Thr Ile Ser Ala Asp Lys Ser Ile Ser Thr Ala Tyr
65                  70                  75                  80

Leu Gln Trp Asn Asn Leu Lys Ala Ser Asp Thr Gly Met Tyr Tyr Cys
                85                  90                  95

Ala Thr Gln Gln Ser Asn Pro Tyr Asp Ser Gly Ser Tyr Trp Tyr Phe
            100                 105                 110

Asp Ser Trp Gly Gln Gly Thr Leu Val Thr Val Ser Ser
        115                 120                 125

<210> SEQ ID NO 18
<211> LENGTH: 107
<212> TYPE: PRT
<213> ORGANISM: Homo sapiens

<400> SEQUENCE: 18

Asp Ile Val Met Thr Gln Ser Pro Pro Ser Leu Ser Ala Ser Ile Gly
1               5                   10                  15

Asp Arg Val Thr Ile Thr Cys Arg Ala Ser Gln Gly Ile Arg Asn Phe
            20                  25                  30

Leu Ala Trp Tyr Gln Gln Lys Pro Gly Lys Val Pro Lys Leu Leu Ile
        35                  40                  45
```

Tyr Ala Ala Ser Thr Leu Gln Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Val Ala Thr Tyr Tyr Cys Gln Lys Tyr Phe Ser Ala Pro Pro
                85                  90                  95
Asp Phe Gly Gln Gly Thr Arg Leu Glu Ile Lys
            100                 105

<210> SEQ ID NO 19
<211> LENGTH: 8
<212> TYPE: PRT
<213> ORGANISM: Homo sapiens

<400> SEQUENCE: 19

Gly Gly Pro Phe Thr Gly Ser Tyr
1               5

<210> SEQ ID NO 20
<211> LENGTH: 7
<212> TYPE: PRT
<213> ORGANISM: Homo sapiens

<400> SEQUENCE: 20

Val Ser Gln Ser Gly Ser Thr
1               5

<210> SEQ ID NO 21
<211> LENGTH: 12
<212> TYPE: PRT
<213> ORGANISM: Homo sapiens

<400> SEQUENCE: 21

Ala Arg Leu Thr Lys His Tyr Ile Asn Ser Ala Tyr
1               5                   10

<210> SEQ ID NO 22
<211> LENGTH: 118
<212> TYPE: PRT
<213> ORGANISM: Homo sapiens

<400> SEQUENCE: 22

Gln Val Gln Leu Gln Glu Ser Gly Ala Gly Leu Val Lys Pro Ser Glu
1               5                   10                  15
Thr Leu Ser Leu Thr Cys Gly Val Ala Gly Gly Pro Phe Thr Gly Ser
                20                  25                  30
Tyr Leu Ser Trp Ile Arg Gln Pro Pro Gly Lys Gly Leu Glu Trp Ile
            35                  40                  45
Gly Glu Val Ser Gln Ser Gly Ser Thr Ser Tyr Asn Pro Ser Leu Lys
    50                  55                  60
Ser Arg Val Thr Ile Ser Val Asp Thr Ser Lys Ser Gln Phe Ser Leu
65                  70                  75                  80
Lys Leu Ser Ser Val Thr Ala Ala Asp Thr Ala Val Tyr Tyr Cys Ala
                85                  90                  95
Arg Leu Thr Lys His Tyr Ile Asn Ser Ala Tyr Trp Gly Gln Gly Thr
            100                 105                 110
Leu Val Thr Val Ser Ser
        115

```
<210> SEQ ID NO 23
<211> LENGTH: 6
<212> TYPE: PRT
<213> ORGANISM: Homo sapiens

<400> SEQUENCE: 23

Gln Ile Ile Gly Ser Trp
1               5

<210> SEQ ID NO 24
<211> LENGTH: 4
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 24

Lys Ala Ser Xaa
1

<210> SEQ ID NO 25
<211> LENGTH: 9
<212> TYPE: PRT
<213> ORGANISM: Homo sapiens

<400> SEQUENCE: 25

Gln Gln Tyr Asn Ser Tyr Pro Tyr Thr
1               5

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Ile Leu Ser Ala Ser Val Gly
1               5                   10                  15

Asp Arg Val Thr Ile Thr Cys Arg Ala Ser Gln Ile Ile Gly Ser Trp
            20                  25                  30

Leu Ala Trp Tyr Gln Gln Lys Pro Gly Lys Ala Pro Thr Leu Val Ile
        35                  40                  45

Tyr Lys Ala Ser Arg Leu Asp Ser Gly Val Pro Ser Arg Phe Ser Gly
    50                  55                  60

Thr Glu Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 27
<211> LENGTH: 8
<212> TYPE: PRT
<213> ORGANISM: Homo sapiens

<400> SEQUENCE: 27

Gly Phe Gly Ile Gly Ile Tyr Thr
1               5

<210> SEQ ID NO 28
<211> LENGTH: 8
```

```
<212> TYPE: PRT
<213> ORGANISM: Homo sapiens

<400> SEQUENCE: 28

Ile Ser Gly Thr Ser Gln Tyr Ile
1               5

<210> SEQ ID NO 29
<211> LENGTH: 8
<212> TYPE: PRT
<213> ORGANISM: Homo sapiens

<400> SEQUENCE: 29

Val Ser Gly Ser Ser Leu Asp Tyr
1               5

<210> SEQ ID NO 30
<211> LENGTH: 6
<212> TYPE: PRT
<213> ORGANISM: Homo sapiens

<400> SEQUENCE: 30

Gln Asn Ile Gly Thr Asn
1               5

<210> SEQ ID NO 31
<211> LENGTH: 4
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 31

Gly Ala Ser Xaa
1

<210> SEQ ID NO 32
<211> LENGTH: 9
<212> TYPE: PRT
<213> ORGANISM: Homo sapiens

<400> SEQUENCE: 32

Tyr Gln Asn Tyr Asn Ser Pro Lys Thr
1               5

<210> SEQ ID NO 33
<211> LENGTH: 115
<212> TYPE: PRT
<213> ORGANISM: Homo sapiens

<400> SEQUENCE: 33

Glu Val Gln Leu Val Glu Ser Gly Gly Gly Arg Val Lys Pro Gly Gly
1               5                   10                  15

Ser Leu Arg Leu Ser Cys Ser Val Ser Gly Phe Gly Ile Gly Ile Tyr
            20                  25                  30

Thr Met Asn Trp Val Arg Gln Ala Pro Gly Lys Gly Leu Glu Trp Val
        35                  40                  45

Ser Ser Ile Ser Gly Thr Ser Gln Tyr Ile Tyr Tyr Ala Asn Ser Val
    50                  55                  60

Arg Gly Arg Phe Thr Ile Ser Arg Asp Asn Ala Glu Asn Ser Leu Tyr
65                  70                  75                  80
```

```
Leu Gln Leu Asn Asn Leu Arg Ala Glu Asp Thr Ala Leu Tyr Tyr Cys
                85                  90                  95

Val Ser Gly Ser Ser Leu Asp Tyr Trp Gly Gln Gly Thr Leu Val Thr
            100                 105                 110

Ile Ser Ser
        115

<210> SEQ ID NO 34
<211> LENGTH: 107
<212> TYPE: PRT
<213> ORGANISM: Homo sapiens

<400> SEQUENCE: 34

Asp Ile Gln Leu Thr Gln Ser Pro Ser Ser Leu Ser Ala Ser Val Gly
1               5                   10                  15

Gly Arg Val Thr Ile Thr Cys Arg Ala Ser Gln Asn Ile Gly Thr Asn
            20                  25                  30

Leu Asn Trp Phe Gln Gln Lys Pro Gly Thr Ala Pro Asn Leu Leu Ile
        35                  40                  45

Tyr Gly Ala Ser Thr Leu Gln Ser Gly Val Pro Ser Arg Phe Ser Gly
    50                  55                  60

Ser Gly Ser Gly Thr Thr Phe Thr Leu Thr Ile Asp Ser Leu Gln Pro
65                  70                  75                  80

Glu Asp Phe Ala Thr Tyr Tyr Cys Tyr Gln Asn Tyr Asn Ser Pro Lys
                85                  90                  95

Thr Phe Gly Gln Gly Thr Lys Val Asp Leu Lys
                100                 105
```

HUMAN NEUTRALIZING ANTI-TETANUS TOXIN MONOCLONAL ANTIBODY AND ITS APPLICATIONS

This application requests for the priority date of the following Chinese patent applications: Application #2017114867326, entitled "A fully native human neutralizing monoclonal antibody against tetanus toxin and its applications" filed on Dec. 29, 2017; Application #201711486693X, entitled "Preparation of neutralizing antibody against tetanus toxin and its applications" filed on Dec. 29, 2017; Application #2017114829697, entitled "an fully native human neutralizing antibody against tetanus toxin" filed on Dec. 29, 2017, and Application #201810420730.5 entitled "A neutralizing antibody against tetanus toxin and its applications" filed on May 4, 2018. All above Chinese patent applications are incorporated by reference herein.

FIELD OF TECHNOLOGY

This invention belongs to the field of Cellular Immunology and Genetic Engineering, and relates to a fully native human neutralizing monoclonal antibody against tetanus toxin and its applications.

BACKGROUND OF THE INVENTION

Tetanus is an acute disease characterized by muscle spasms caused by a neurotoxin produced by *Clostridium tetani* after its invasion into a body through a wound and reproduction under anaerobic environment. Serious patients may die because of laryngeal spasm or severe secondary lung infection. The death rate can be as high as 20-50% among the newborns and serious patients. Every year there are about one million deaths globally caused by tetanus, mostly in undeveloped countries and regions. Clinically tetanus is categorized in four types: local tetanus, cephalic tetanus, generalized tetanus and neonatal tetanus.

*C. tetani* is strict anaerobic bacteria, and its spores are extremely hardy and are resistant to draught, heat and antiseptics but sensitive to iodine solution or neutral glutaraldehyde solution, and can be killed by these reagents in short period of time. *C. tetani* can produce two kinds of exotoxins: tetanus hemolytic toxin which causes hemolysis, and tetanus spastic toxin which is the commonly known tetanus toxin.

Tetanus toxin is a protein produced and secreted by *C. tetani*, consisted with 1315 amino acids and with a molecular weight of 150,700 Da. The estimated lethal dose for tetanus toxin is about 0.25 ng/kg. Tetanus toxin is expressed as a single chain protein inside of the bacteria cell, and then is cleaved by protein enzymes into a light chain and a heavy chain coupled together by a disulfide bond. According to its in vivo functions, the tetanus toxin molecule is divided into A, B and C three regions: the light chain fragment is A fragment, N-terminal half of the heavy chain is B fragment, and the other half of heavy chain is C fragment.

Generally, the mechanisms of tetanus toxin are three steps: binding, transport and action. Researches have shown that C fragment of tetanus toxin can bind to toxin receptor, which is generally believed as a ganglioside. The C fragment has the function of retrograde axonal transport to the central nervous system, and has been used to develop subunit vaccines. B fragment can form an ion channel through artificial phospholipid bilayer, transporting the active fragment of toxin into a cell. The Fragment A is a Zn protease, with proteolysis activity, and can breakdown membrane proteins involving protein-vesicular transportation of neurotransmitters. This inhibits the release of neurotransmitters and causes the continuous transmission of excitatory impulse, resulting into clinic symptom of violent spastic paralysis. However, direct isolation and purification of C fragment from tetanus toxin have many shortcomings: high toxicity of tetanus toxin, possible transmission by spores, complex processes for culture and isolation, low recovery rate and certain degree of risk.

In early days, tetanus toxoid was used for prevention and treatment of tetanus as immunoreagents, but with quite some adverse reactions, such as high sensitization. In the 60s of $20^{th}$ century, developed countries in Europe and America have developed human tetanus immunoglobin (HTIG). The production of HTIG in China began in 80s, and current production of HTIG still cannot meet the demands from the market, mainly TAT from horse serum occupies the majority of market share. Humanized HTIG has overcome the adverse reactions such as sensitization reaction caused by the clinic usage of horse serum TAT, and significantly improved the prevention and treatment of tetanus. But the human bloods are scarce sources with high cost, also with the risk of exogenous virus contamination, the industrial production and clinical use of HTIG have been largely limited.

Currently, there are reports on transforming mouse monoclonal antibody to produce genetically engineered and humanized tetanus toxin, but those are still at the stage of lab experimentation. Recently, as the rapid development of genetic engineering technology, it becomes possible to produce humanized human antibody using genetic engineering technology. The humanized human antibody produced via genetic engineering may reduce or eliminate the sensitization reaction caused by exnogeneic serum. It may also resolve the problems of insufficient source of human blood for human immunoglobulin production or the potential virus contamination. This has become the focus of current research.

DESCRIPTION OF INVENTION

In order to improve the shortage of current technology, the main purpose of this invention is to provide an fully native human neutralizing monoclonal antibody against tetanus toxin and its antigen binding fragment without immunogenicity or exogenous virus contamination but with high affinity, high specificity and high efficiency, also to provide encoding sequences for the antibody, cell lines for production of the antibody, and methods and applications for using the antibody for diagnosis, prevention or treatment.

In one aspect, the invention provides an fully native human neutralizing monoclonal antibody against tetanus toxin and an antigen-binding fragment thereof, wherein the neutralizing monoclonal antibody comprises at least a heavy chain variable domain (VH) having three CDRs and at lease a light chain variable domain (VL) having three CDRs:

wherein the CDR1, CDR2 or CDR3 of the VH comprising an amino acid sequence set forth in any one of SEQ ID NO:1, 2, 3, 9, 10, 11, 19, 20, 21, 27, 28, or 29, or said sequences having a replacement, a deletion or an insertion of one or more amino acids thereof, or an amino acid sequence having at least 80% homology to the sequence set forth in SEQ ID NO:1, 2, 3, 9, 10, 11, 19, 20, 21, 27, 28, or 29 and having the same or similar functions; and the CDR1, CDR2 or CDR3 of the VL comprising an amino acid sequence set forth in any one of SEQ ID NO: 4, 5, 6, 13, 14, 15, 23, 24, 25, 30, 31, or 32, or said amino acid sequence having a a replacement, a deletion or an insertion of one or more amino acids thereof, or an amino acid sequence having at least 80% homology to the sequence set forth in SEQ ID NO: 4, 5, 6, 13, 14, 15, 23, 24, 25, 30, 31, or 32 and having the same or same functions.

Preferably,
wherein the CDR1, CDR2 or CDR3 of VH of the neutralizing monoclonal antibody comprising the amino acid sequence set forth in SEQ ID NO: 1, SEQ ID NO: 2, or SEQ ID NO: 3; wherein the CDR1, CDR2 or CDR3 of VL comprising the amino acid sequence set forth in SEQ ID NO: 4, SEQ ID NO: 5, or SEQ ID NO: 6;

wherein the CDR1, CDR2 and CDR3 of VH of the neutralizing monoclonal antibody comprising the amino acid sequence set forth in SEQ ID NO: 9, SEQ ID NO: 10, or SEQ ID NO: 11; wherein the CDR1, CDR2 or CDR3 of VL comprising the amino acid sequence set forth SEQ ID NO: 13, SEQ ID NO: 14, or SEQ ID NO: 15;

wherein the CDR1, CDR2 or CDR3 of VH of the neutralizing monoclonal antibody comprising the amino acid sequence set forth in SEQ ID NO: 19, SEQ ID NO: 20, or SEQ ID NO: 21; wherein the CDR1, CDR2 and CDR3 of VL comprising the amino acid sequence set forth in SEQ ID NO: 23, SEQ ID NO: 24, or SEQ ID NO: 25;

wherein the CDR1, CDR2 and CDR3 of VH of the neutralizing monoclonal antibody comprising the amino acid sequence set forth in SEQ ID NO: 27, SEQ ID NO: 28, or SEQ ID NO: 29; wherein the CDR1, CDR2 and CDR3 of VL comprising the amino acid sequence set forth in SEQ ID NO: 30, SEQ ID NO: 31, or SEQ ID NO: 32.

Further, the VH of the neutralizing monoclonal antibody comprises an amino acid sequence set forth in any one of SEQ ID NO.7, SEQ ID NO.17, SEQ ID NO.22, and SEQ ID NO.33, or said amino acid sequence having a replacement, a deletion or an insertion of one or more amino acids thereof, or an amino acid sequence having at least 80% homology to the amino acid sequence set forth in SEQ ID NO:7, SEQ ID NO:17, SEQ ID NO:22, or SEQ ID NO:33 and having the same or similar functions; and the VL of the neutralizing monoclonal antibody comprising an amino acid sequence set forth in any one of SEQ ID NO:8, SEQ ID NO:18, SEQ ID NO:26, or SEQ ID NO:34, or said amino acid sequence having a replacement, a deletion or an insertion of one or more amino acids thereof, or an amino acid sequence having at least 80% homology to the amino acid sequence set forth in SEQ ID NO:8, SEQ ID NO:18, SEQ ID NO:26, or SEQ ID NO:34 and having the same or similar functions;

Preferably,
wherein the VH of the neutralizing monoclonal antibody comprising the amino acid sequence is set forth in SEQ ID NO: 7, and the VL comprising the amino acid sequence set forth in SEQ ID NO: 8;

And the VH of the neutralizing monoclonal antibody comprises the amino acid sequence set forth in SEQ ID NO.17, and the VL of the neutralizing monoclonal antibody comprises the amino acid sequence set forth in SEQ ID NO.18;

And the VH of the neutralizing monoclonal antibody comprises the amino acid sequence set forth in SEQ ID NO.22, and the VL of the neutralizing monoclonal antibody comprises the amino acid sequence set forth in SEQ ID NO.26;

And the VH of the neutralizing monoclonal antibody comprises the amino acid sequence set forth in SEQ ID NO.33, and the VL of the neutralizing monoclonal antibody comprises the amino acid sequence set forth in SEQ ID NO.34.

Furthermore, the neutralizing monoclonal antibody or the antigen-binding fragment thereof of this invention binds immune-specifically with tetanus toxin, and the neutralizing monoclonal antibody or the antigen-binding fragment thereof dissociates from tetanus toxin and/or *Clostridium tetani* at an equilibrium dissociation constant (KD) no higher than $10^{-6}$M.

Preferably, the heavy chain type of the neutralizing monoclonal antibody of this invention is IgG1, IgG2, IgG3, or Ig4, and more preferably, IgG1.

Preferably, the light chain type of the neutralizing monoclonal antibody of this invention is k or l.

The neutralizing monoclonal antibody of this invention comprises not only a variable region but also a constant region.

Preferably, the constant region of the neutralizing monoclonal antibody of this invention is the one from any of human IgG1, IgG2, IgG3 or IgG4.

The anti-tetanus toxin antibody or its antigen binding fragment of this invention is preferable humanized antibody, comprising (not limited to) single chain Fv (scFv), Fab, Fab', F(ab')2, Fv, dsFv, diabody, Fd or Fd' fragment.

The neutralizing monoclonal antibody or the antigen-binding fragment thereof of this invention also comprises a peptide adaptor, and preferably, the peptide adaptor comprises about 1-50 amino acids.

In another aspect, this invention provides a combination, and the combination which is consisted above described neutralizing monoclonal antibody or the antigen-binding fragment thereof of this invention, and labeling conjugated to the neutralizing monoclonal antibody or the antigen-binding fragment thereof of this invention, such as testable part and reagents. The labeling is directly conjugated covalently or non-covalently to the neutralizing monoclonal antibody or the antigen-binding fragment thereof of this invention. Also, the labeling can be conjugated through one or more adaptors to the neutralizing monoclonal antibody or the antigen-binding fragment thereof of this invention. The technics for conjugating labeling to the neutralizing monoclonal antibody or the antigen-binding fragment thereof of this invention are well known to technicians of this field. The testable part and/or reagents of the labeling include free enzymes, prosthetic groups, fluorescent materials, bioluminescent materials, radioactive materials, positron emitting materials, and non-radioactive paramagnetic metal ions.

In another aspect, this invention provides a complex, comprising the above described neutralizing monoclonal antibody or its antigen-binding fragment, and a chemical or a biological labeling covalently linked to the above described neutralizing monoclonal antibody or its antigen-binding fragment.

Preferably, said chemical labeling including isotopic labeling, immunotoxin labeling, or chemical drug labeling; and said biological labeling including biotin labeling, avidin labeling, enzyme labeling, fluorescent labeling, or electron transfer agent labeling.

In another aspect, this invention provides a conjugate, comprising the above described neutralizing monoclonal antibody or its antigen-binding fragment, and/or above described conjugate, and/or above described composition coupled to a solid or semi-solid medium.

The examples of solid or semi-solid medium include enzyme-coated plate (ELISA plate), magnetic or non-magnetic immunosphere or immunogranules, and cell dispersing agent. Examples of the cell dispersing agent includes olyvinyl-pyrrolidone-coated colloidal silicon dioxide, polysaccharide and sodium amidotrizoate or its derivatives.

In another aspect, this invention provides a composition comprising the above described neutralizing monoclonal antibody or its antigen-binding fragment, and/or above described combination, and/or above described complex, and/or above described conjugate.

The composition includes drug composition and diagnostic composition.

The above described drug composition also includes acceptable pharmaceutic adjuvant. The acceptable pharmaceutic adjuvants are those adjuvant or diluent agent with little significant irritation to body and no effect to eliminate the biological activities of pharmaceutic compounds. Examples include saline, sterile water, Ringer's solution, buffered saline, glucose solution, maltodextrin solution, glycerin, ethanol, or a mixture of two or more thereof. If necessary, the drug composition described in this invention may include other regularly used additives, such as antioxidants, buffers, bacteriostatic, dispersants, surfactants, adhesives and lubricants. It can also be made into different dosage forms, such as injectable preparations like solutions, suspensions or emulsions, pills, capsules, granules or tablet.

The drug composition must be sterile and stable in production or storage. When producing sterile powder for injectable solutions, the preferred method is vacuum drying or frozen drying. Vacuum drying or frozen drying can transform sterilized filtered solutions into powders while keeping the activity of the pharmaceutic compounds. Optionally, pharmaceutically acceptable excipients may be added into a solution of the drug combination of composition of this invent to generate injectable unit dosage form. Preferably, the pharmaceutically acceptable excipients used in this invention are suitable for high drug concentration, are able to keep adequate fluidity, and if necessary, are able to delay drug absorption.

Several factors influence the choices of the best route of administration, including the physical and chemical properties of the active ingredients of the drug combination of compositions, the seriousness and urgency of symptoms, and the relationships between the blood concentration of the active ingredients and expected drug effects. For example, adjuvant may be added during the preparation of the neutralizing monoclonal antibody of this invention, which may protect the antibody from fast release (such as release-control adjuvant), such adjuvant may include implants, patches, or microcapsules. Polymers that is biodegradable and biocompatible can be used in this invention, such as ethylene vinyl acetate, polyanhydride, polyglycolic acid, collagen, polyester or polylactide. Furthermore, the neutralizing monoclonal antibody may mix with compounds or materials that can protect the antibody from loss of bioactivity, or administrated together with such compounds or materials. For example, the neutralizing monoclonal antibody may be administrated together with appropriate adjuvant such as liposomes or diluents.

The route of administration of drug composition of this invention may be oral or parenteral administration. The preferred route is intravenous injection, but not limited to it.

The oral dosage form can be tablet, lozenge, sugar lozenge, water-based or on-based suspension, power, granule, emulsion, hard capsule, soft capsule, syrup, pill, sugar-coated pill, liquid, gel, or ointment. These may also contain some excipients, including but not limited to, granulating agent, disintegrating chemical, adhesive, lubricant, preservative, colorant, blending agents or sweetener, vegetable oil or mineral oil, humectant, and thickening agent.

The parenteral dosage form may be water based or non-water based sterile isotonic solution for injection or perfusion, or suspension. Said solution or suspension may be agents that are not toxic to subjects at an administrative concentration and dosage, such as 1, 3-butanediol, Ringer's solution, Hank's solution, isotonic sodium chloride solution, oil, fatty acid, localized anesthetic, preservative, buffer solution, agent increasing viscosity or solubility, water soluble antioxidant, oil soluble antioxidant and metal chelating agent.

The said drug composition may also include one or more other therapeutic agents, such as antibody, small molecular weight compounds, organic compounds, inorganic compounds, enzymes, or polynucleotides.

In another aspect, this invention provides a testing product, comprising the above described neutralizing monoclonal antibody or its antigen-binding fragment, and/or the combination, and/or the complex, and/or the conjugate, and/or the composition.

The testing product of this invention may be used to detect tetanus toxin or *Clostridium tetani* infection. Specifically, the testing product of this invention measures the level of tetanus toxin in fluid, cell or tissue sample through antibody. At the same time, the testing product provided in the examples of this invention is able to compare the measured tetanus toxin level with the control level. A higher measured tetanus toxin level than control level indicates infection by tetanus toxin. Preferably, the cell or tissue samples are from human subject, and the samples may include blood, urine, saliva, lavage sample or lymphoid tissue.

In another aspect, this invention provides a DNA molecule encoding the above described neutralizing monoclonal antibody or the antigen-binding fragment thereof.

Said DNA molecule may be obtained using any known methods of this field of technology. For example, if the nucleotide sequence of the antibody is known, said antibody encoding DNA molecule may be assembled with chemically synthesized oligonucleotides.

Or, said antibody encoding DNA molecule may be generated from nucleotides from proper source. If it is unable to obtain a clone of said antibody encoding DNA molecules, but the sequence of said antibody is known, then the immunoglobulin DNA molecules may be chemically synthesized, or may be amplified by PCR using synthesized 3'-an 5'-primers capable of hybridizing with said sequence; or to obtain said encoding DNA molecules using cloning with an oligonucleotide probe which is specific for the said encoding sequence, for example, to isolate encoding cDNA clone from a cDNA library. Then the amplified DNA molecules by PCR may be cloned into a replicable cloning vector using any known methods of this field.

In another aspect, this invention provides a recombinant expression vector, comprising above described DNA molecule.

The expression vector for construction of said recombinant expression vector may include but not limited to MarEx expression vector by Celltrion Inc., market widely available pCDNA vector, F, R1, RP1, Col, pBR322, ToL, Ti vector, cosmid vector, phage such as I phage, M13 phage, Mu phage, P1 phage, P22 phage, Qm phage, T-even phage, T2 phage, T4 phage, T7 phage, plant virus vectors. Any of the expression vectors known to the technicians in the field may be used, and selection of the expression vectors depends on properties of selected host cells. The expression vector may be introduced into a host cell by (but not limited to) for example, calcium phosphate transfection, virus infection, DEAE-dextran induced transfection, liposome transfection or electroporation transfection. Any technicians in this field may choose or use a method suitable to introduce any expression vectors into any host cells. Preferably, said expression vector contains one or more selection marker, but not limited by this, a vector without selection marker may also be used. The choice for selection of markers depends on the selected host cell as well known by the technicians in this field, but this is not critical for this invention.

In order to benefit the purification of the DNA molecules of this invention, a tag sequence may be inserted into the expression vector. Examples of tag sequences include but not limited to, six histidine tag, hemagglutinin tag, myc tag or FLAG tag. Any tag that is known to the technicians of this field to benefit the purification may be used in this invention.

In another aspect, this invention provides a recombinant cell, said recombinant cell results from transformation or transfection of a host cell with above described expression vector.

Any cell that is known to the technicians of this field may be used as a host cell. The host cell in this invention may include but not limited to, microorganism, such as bacterial transformed with recombinant phage DNA containing antibody encoding sequence, plasmid DNA or cosmid DNA (i.e. *E. coli, B. subtilis*), yeast transformed with a recombinant yeast expression containing antibody encoding sequence such as *Saccharomyces* and *Pichia*, insect cell system infected with a recombinant virus expression vector such as baculovirus, plant cell system infected with a recombinant virus expression vector (such as CaMV or TMV) containing antibody encoding sequence, or a mammal cell system (such as COS, CHO, BHK, 293, 3T3 cell) transfected with a recombinant expression vector with a promoter from mammal cell genome (such as metallothionein promoter) or from a mammal cell virus (such as adenoviral late promoter, or poxvirus 7.5 K promoter).

In another aspect, this invention provides a method for detection of the existence or the level of tetanus toxin or *Clostridium tetani* in a sample, using the neutralizing monoclonal antibody or the antigen-binding fragment thereof. In a preferable example, the neutralizing monoclonal antibody or the antigen-binding fragment thereof comprises detectable labeling. In another preferable example, the said method uses a detectable labeling coupled a second antibody to detect the neutralizing monoclonal antibody or the antigen-binding fragment thereof of this invention. The said method may be for diagnostic purpose or non-diagnostic purpose (for example the sample may be cell sample of sample from a patient).

In another aspect, this invention provides a method to diagnose whether a subject is infected with tetanus toxin or *Clostridium tetani*, including detection of the existence of tetanus toxin or *Clostridium tetani* in a subject's sample. In a preferable example, the neutralizing monoclonal antibody or the antigen-binding fragment thereof comprises detectable labeling. In another preferable example, the said method uses a detectable labeling coupled second antibody to detect the neutralizing monoclonal antibody or the antigen-binding fragment thereof of this invention.

In another aspect, this invention provides a method to neutralize the toxicity of tetanus toxin in a sample, including mixing the tetanus toxin containing sample with the neutralizing monoclonal antibody or the antigen-binding fragment thereof of this invention. The said method may be for diagnostic purpose or non-diagnostic purpose (for example the sample may be cell sample of sample from a patient).

In another aspect, this invention provides an application of the above described neutralizing monoclonal antibody or its antigen-binding fragment, and/or the combination, and/or the complex, and/or the conjugate, and/or the composition for manufacture of the testing product for detection of tetanus toxin or *Clostridium tetani* infection.

Preferably, said testing product is a detection kit, an ELISA plate, or a chip.

In another aspect, this invention provides an application of the above described neutralizing monoclonal antibody or its antigen-binding fragment, and/or the combination, and/or the complex, and/or the conjugate, and/or the composition for manufacture for production of drugs or medications, and/or prevention or treatment of diseases caused by tetanus toxin or *Clostridium tetani* infection.

In another aspect, this invention provides an application of above described DNA molecule, recombinant expression vector, recombinant cell for production of drugs or medications roe prevention or treatment of diseases caused by tetanus toxin or *Clostridium tetani* infection.

As used in this Description, the term "antibody" is defined as a protein molecule acting as a receptor specifically recognizing an antigen, including immunoglobulin reacting with specific antigen, including the whole antibody, dimer, trimer o polymer of antibody, bispecific antibody, chimeric antibody, recombinant or engineered antibody, and a fragment thereof, so long as the fragment contains the antigen binding region.

As used in this Description, the term "antibody" is defined as a protein molecule acting as a receptor specifically recognizing an antigen, including immunoglobulin reacting with specific antigen, including the whole antibody, dimer, trimer o polymer of antibody, bispecific antibody, chimeric antibody, recombinant or engineered antibody, and a fragment thereof, so long as the fragment contains the antigen binding region.

A whole antibody may belong a type of IgA, IgD, IgE, IgM and IgG, and IgG may include IgG1, IgG2, IgG3 and IgG4 subtype. Antibody fragment is the region with antigen binding function, including Fab, Fab', F(ab') 2 and Fv. A Fab fragment contains a light chain variable region and a heavy chain variable region, light chain constant region and first heavy chain constant region (CH1 domain), also an antigen biding site. Fab' differs from Fab for its hinge region. The c-terminus of heavy chain CH1 domain contains at least a cysteine residue. F(ab') 2 antibody is resulted from the formation of disulfide bond between the cysteine residues located in the hinge region of Fab' fragment. Fv (variable fragment) is the least antibody fragment only containing a heavy chain variable region and a light chain variable region. Double chain Fv (dsFv) contains a heavy chain variable region coupled to a light chain variable region through disulfide bond. Single chain Fv (scFv) usually contains a heavy chain variable region coupled to a light chain variable region through a peptide adaptor. Such antibody fragment may result from proteases lysis (such as using papain to zymolyze a whole antibody to obtain F(ab') 2 fragment). Preferably, an antibody fragment may be constructed using recombinant genetic engineer technology.

The term "neutralizing monoclonal antibody" is defined as a monoclonal antibody with neutralizing activity. Monoclonal antibodies are antibodies with a single molecular composition with unique binding specificity and affinity to a specific epitope. Typically, immunoglobulin contains a heavy chain and a light chain. Both heavy chain and light chain contain a constant region and a variable region (a region is also called a domain). Each light chain or heavy chain contains four framework regions, separated by three variable regions, also called complementarity determining regions (thereafter, "CDR"). CDR is mainly responsible for binding to antigen epitope. The CDRs in each chain are usually CDR1, CDR2 and CDR3, as numbered successively from N-terminus.

The neutralizing monoclonal antibody of this invention also includes its functional variants, said functional variants are able to bind tetanus toxin or its fragment, and have the neutralizing activity against the said subtype or fragment of tetanus toxin.

More specifically, such functional variants may include derivatives having basically the similar primary sequence with the neutralizing monoclonal antibody of this invention but with chemical or biochemical modifications that are not found in the neutralizing monoclonal antibody of this invention. Said modifications may include acetylation, acylation, covalently coupling with nucleotide or nucleotide derivative, covalently coupling with lipid or lipid derivative, crosslinking, disulfide bond formation, glycosylation, hydroxylation, methylation, oxidation, polyethylene glycosylation, protein hydrolysis and phosphorylation.

Optionally, the functional variants may include the following neutralizing monoclonal antibodies: an amino acid sequence with one or more replacement, insertion, or deletion, or the combination thereof, of amino acids as compared with the amino acid sequence of parent neutralizing monoclonal antibody. Further, the functional variants may have truncated amino acid sequence at its N-terminal end or C-terminal end or both ends. The functional variants may have the same or different, higher or lower affinity as compared with the parent neutralizing monoclonal antibody, but still bind tetanus toxin or its fragment. For example, a functional variant of this invention may have increased or reduced binding affinity with tetanus toxin or its fragment.

Preferably, the amino acid sequence that may be modified include but not limited to framework region, highly variable region, especially variable region of CDR3. In general, a light chain and a heavy chain contain three highly variable regions (including three CDRs) and more conserved regions (the so-called framework region, FR). A highly variable region contains amino acid residues from CDR and highly variable loop. Technicians of this field may use well-known computer algorithms, such as Gap or Bestfit to compare amino acid sequences, to define the same or similar residues. Some generally used methods in molecular biology (such as PCR, oligonucleotide-directed mutagenesis, site-directed mutagenesis) may be employed to modify parent neutralizing monoclonal antibody or its fragment, or another option is to generate functional variants by organic synthesis.

The technicians of this field will also understand that the modifications of amino acid sequence of anti-tetanus toxin antibodies covered in this invention, and as an example, modified binding affinity or other biological properties of the antibodies. The amino acid variants of anti-tetanus toxin antibody may be produced with introducing appropriate nucleotide changes to the anti-tetanus toxin antibody encoding sequence, or by peptide synthesis. Such modifications may include (for example) replacement, deletion or insertion of residues. The deletion, insertion, replacement of residues, or combination thereof, complete the final construction of functional variants, the restrictions of which depends on the requested functional characters of the final constructions. Changes of amino acid may also change the post-translation process, such as the numbers or sites of glycosylation.

The advantages and beneficial effects of this invention are the followings:

This invention develops fully native human neutralizing monoclonal antibodies against tetanus toxin through a high throughput fully native human monoclonal antibody systematic development platform.

The fully native human neutralizing monoclonal antibodies against tetanus toxin developed in this invention is applicable to the prevention and treatment of *Clostridium tetani* infection.

The fully native human neutralizing monoclonal antibodies against tetanus toxin developed in this invention is applicable to the detection of *Clostridium tetani* infection.

The fully native human neutralizing monoclonal antibodies developed in the invention have a high affinity with tetanus toxin, and high neutralizing activities, safe with high effectiveness, free of exogenous virus contamination, and can be widely used in all types of human groups with high industrial utilities.

SPECIFIC METHOD OF USE

Figure 1:
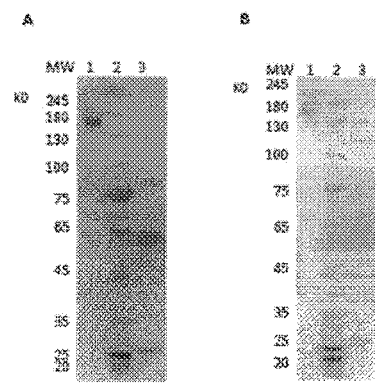
FIG. 1 shows the detection of the expression and purification of TRN0010 antibody using SDS-PAGE and Western Blot, and A for SDS-PAGE, B for Western Blot.
Figure 2:
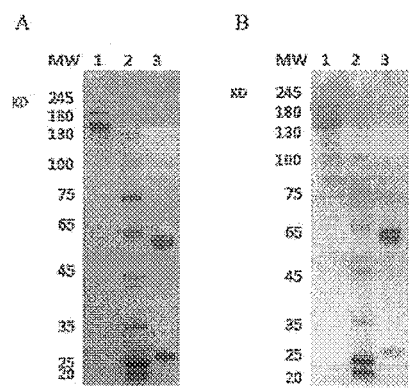
FIG. 2 shows the detection of the expression and purification of TRN0012 antibody using SDS-PAGE and Western Blot, and A for SDS-PAGE, B for Western Blot.
Figure 3:
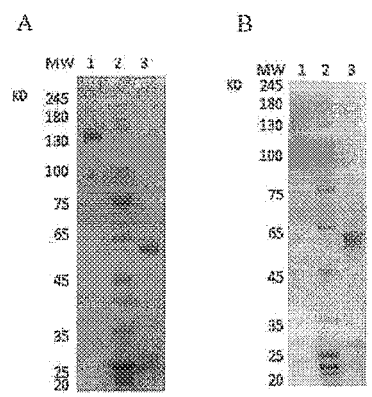
FIG. 3 shows the detection of the expression and purification of TRN0011 antibody using SDS-PAGE and Western Blot, and A for SDS-PAGE, B for Western Blot.
Figure 4:
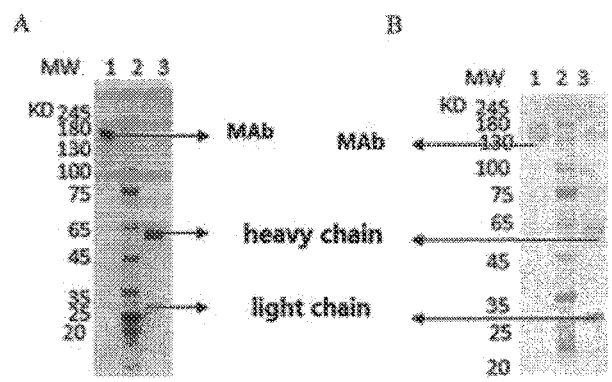
FIG. 4 shows the detection of the expression and purification of TRN0015 antibody using SDS-PAGE and Western Blot, and A for SDS-PAGE, B for Western Blot.
Figure 5:
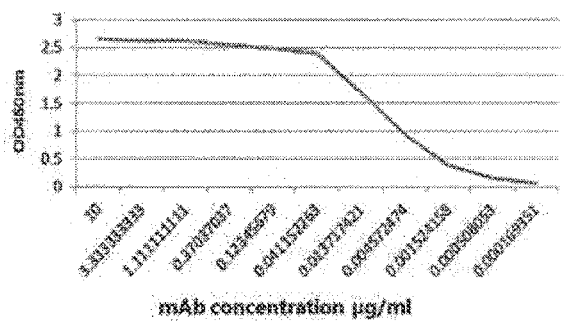
FIG. 5 shows the results for determination of neutralizing activity of TRN0010 antibody using ELISA.
Figure 6:
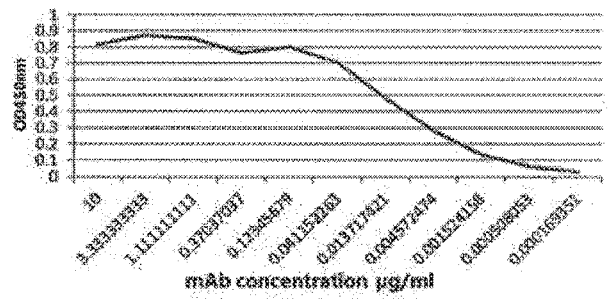
FIG. 6 shows the results for determination of neutralizing activity of TRN0012 antibody using ELISA.
Figure 7:
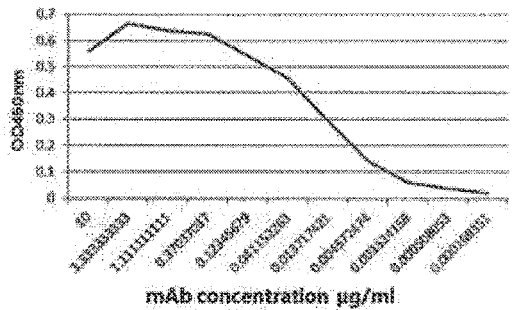
FIG. 7 shows the results for determination of neutralizing activity of TRN0011 antibody using ELISA.
Figure 8:
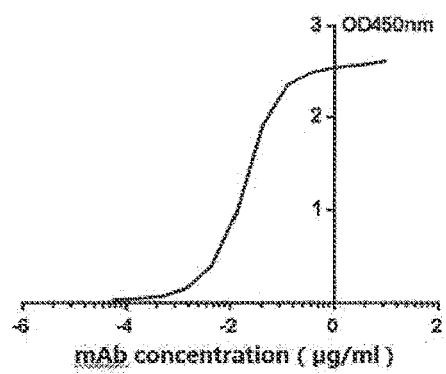
FIG. 8 shows the results for determination of neutralizing activity of TRN0015 antibody using ELISA.
Figure 9:
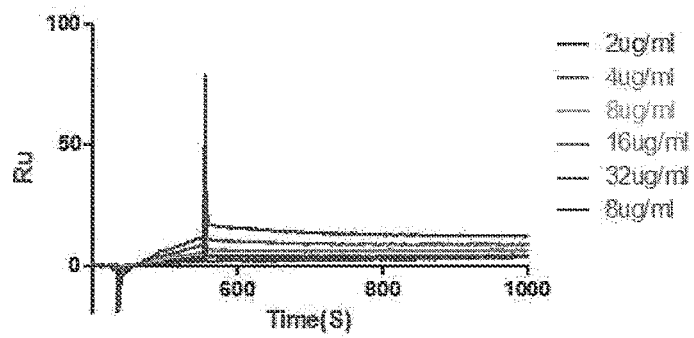
FIG. 9 shows the results for measuring affinity of TRN0010 antibody.
Figure 10:
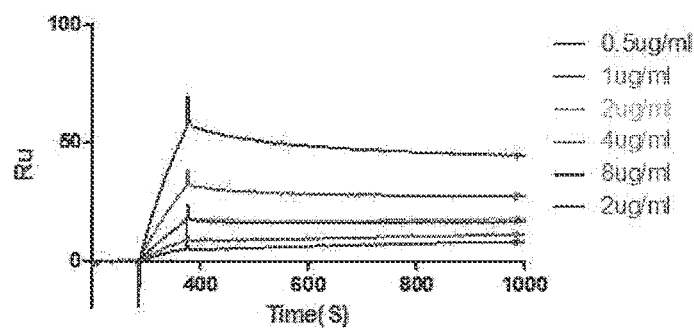
FIG. 10 shows the results for measuring affinity of TRN002 antibody.
Figure 11:
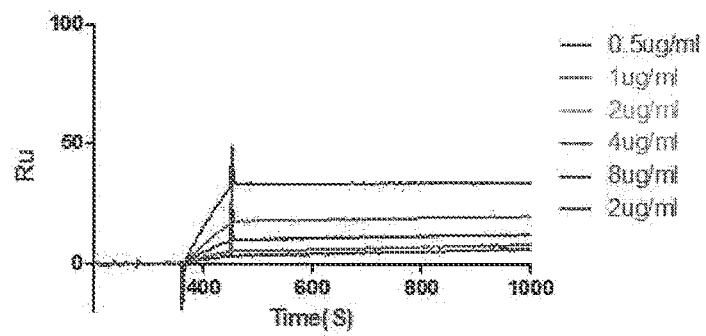
FIG. 11 shows the results for measuring affinity of TRN0011 antibody.
Figure 12:
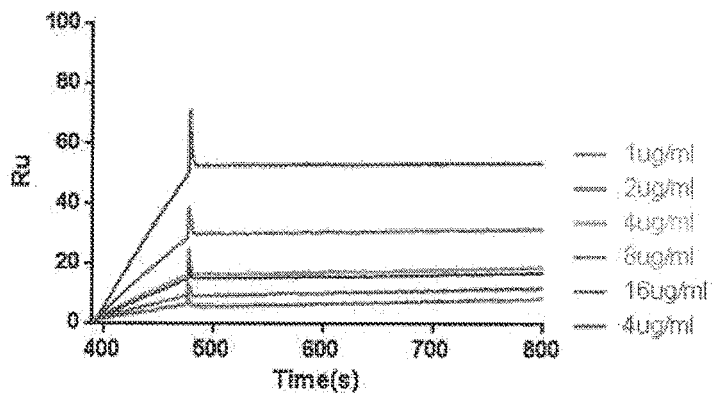
FIG. 12 shows the results for measuring affinity of TRN0015 antibody.
Figure 13:
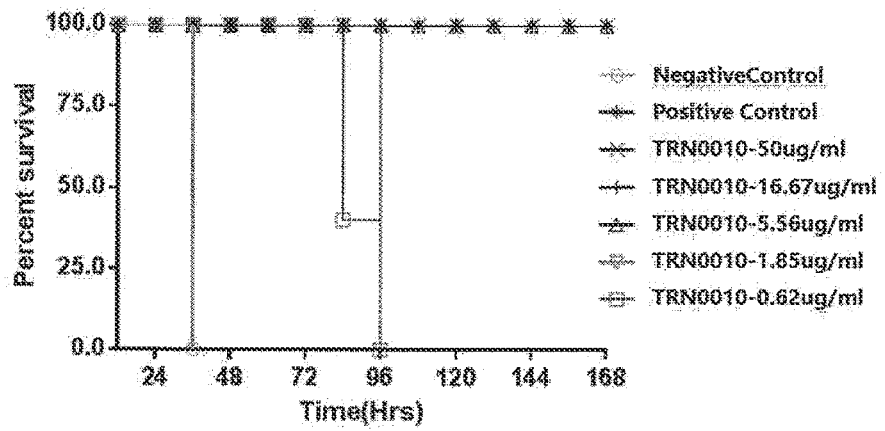
FIG. 13 shows the results for protection effects on animals with TRN0010 antibody.
Figure 14:
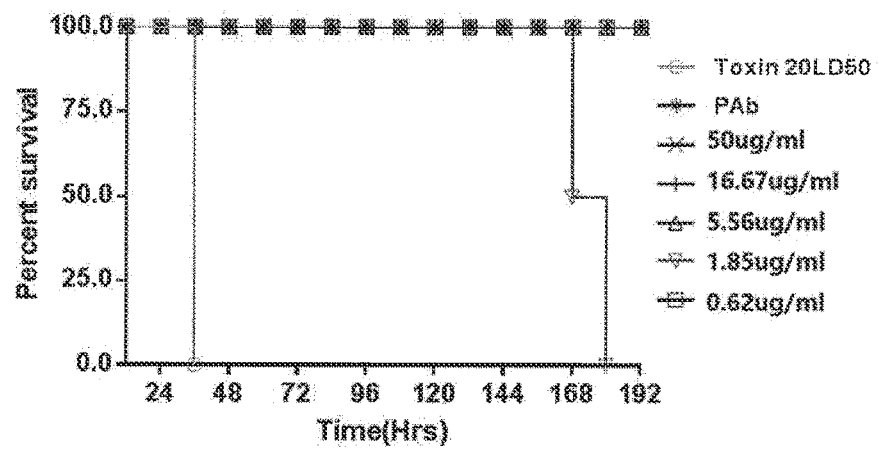
FIG. 14 shows the results for protection effects on animals with TRN0012 antibody.
Figure 15:
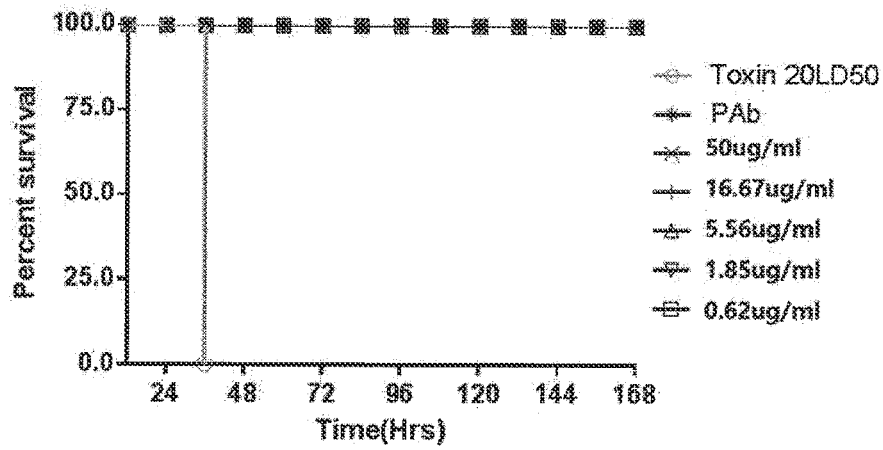
FIG. 15 shows the results for protection effects on animals with TRN0011 antibody.
Figure 16:
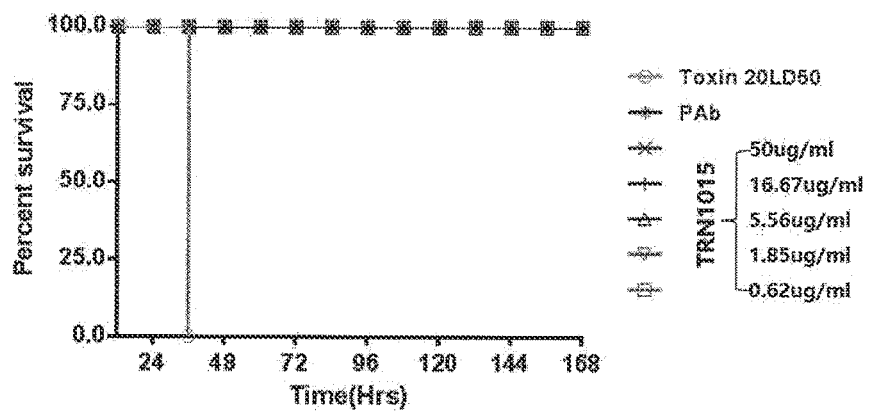
FIG. 16 shows the results for protection effects of TRN0015 antibody against 20 times dose of LD50 tetanus toxin.

The followings further describe this invention in detail with figures and examples. The following examples are only for further description on this invention, and by no means to limit the scope of this invention. Some of the conditions and methods may not disclosed in detail, those conditions and methods are generally described in Molecular Cloning, a Lab Manual by Sambrook et al. of New York Cold Spring Harbor Laboratory Press, 1989, or that recommended by manufacturers.

Example 1. Preparation of all Human Neutralizing Monoclonal Antibody Against Tetanus Toxin 1. Isolation of Cells.

Blood samples were collected from healthy volunteers injected with 1500 IU tetanus toxin, then mononuclear cells (PBMC) were isolated using Ficoll. After cell counts obtained, plasma cells were isolated by FACS using BD FACSria. Intact single cells were placed into 96-well PCR plates, with one single memory B cell per well and then kept in −80° C. freezer for future usage.

2. Isolation of Genes for Variable Regions of Antibody 0.5 mM primers for each subtype constant region of heavy chain and light chain and Superscript III reverse transcriptase were added into the 96-well plate with single B cell, incubated at 37° C. for an hour. PCR was performed under the following parameters: 93° C. 15 min; 95° C. 1 min, 55° C. 1 min, 72° C. 1 min, 30 cycles; 72° C. 10 min; 4° C. 5 min. cDNA products kept at −20° C.

Using above cDNA as template to amplify anti-tetanus toxin fully native human antibody gene. Mixing of 5 ml product of RT reaction, HotStar Taq Plus polymerase (Invitrogen, Carlsbad, Calif.), dNTPs, and 0.5 mm of specific primers for each subtype heavy chain and light chain. Reaction conditions: pre-denaturation at 94° C. 5 min, followed by 35 PCR cycles with the conditions as 94° C.×30s, 55° C.×30s, 72° C.×50s, and at last extension at 72° C. for 7 min. The PCR products were identified with 1% agarose gel electrophoresis 3. Construction of Eukaryotic Expression Vector for Fully Native Human Monoclonal Antibody Against Tetanus Toxin.

(1) taking 2 ml PCR product on 1% agarose gel electrophoresis for detection PCR results. Positive PCR product with complementary pairing between genes for variable regions of heavy chain and light chain were inserted into pcDNA3.3(+/−) expression vector (from Invitrogen) using TA cloning method to construct fully native human anti-tetanus toxin monoclonal antibody expression vector (2) transforming DH5a competent cells with the above expression vector, culturing the transformed cells on ampicillin containing plate at 37° C. overnight.

(3) picking 10 single colonies for PCR confirmation using specific primers, reaction conditions: pre-denaturation at 94° C. for 5 min, denaturation at 94° C. for 30s, annealing at 55° C. for 30s, extension at 72° C. for 1 min 40s, 28 cycles, and at last extension at 72° C. for 5 min.

(4) taking 5 ml PCR product for 1% agarose gel electrophoresis confirmation, and positive transformants were identified.

Results showed that the sequence of constructed anti-tetanus toxin monoclonal antibody heavy/light chain recombinant expression vector was correct.

4. Expression and Identification of Anti-Tetanus Toxin Fully Native Human Neutralizing Monoclonal Antibody Amplifying the plasmids expressing positive antibody heavy and light chain genes in *E. coli* DH5a, and rapidly isolating recombinant plasmids. 293 cells were transfected with anti-tetanus toxin fully native human neutralizing monoclonal antibody expression vector by PolyFect DNA transfection kit according to the instructions from manufacturer. Non-transfected 293 cells served as controls. After 96 hours culture, using ELISA with HPR labeled sheep anti human IgG to detect the expression of anti-tetanus toxin fully native human neutralizing monoclonal antibody and its specific recognition of tetanus vaccine (antigen).

Using tetanus vaccine as antigen and coating a 96 well ELISA plate with 10 times diluted antigen, 100 ml per well at 4° C. overnight. Blocking with blocking solutions at room temperature for 2 hours, then incubating with 100 ml transient expression supernatant as primary antibody at 37° C. for 2 hours, incubating with 1:2000 diluted HRP/anti-His-tag as secondary antibody at 37° C. for 1 h, adding substance color liquid 100 ml per well, placed away from light at room temperature for 5 min, then terminating the reaction with 2M sulfuric acid, and detect at 450 nm wavelength.

Results showed that 293 cells transfected with expression vector plasmids successfully expressed fully native human antibody, and the antibody was able to specifically recognize tetanus vaccine (antigen), while the cultural supernatant from untransfected 293 cells was not able to recognize tetanus vaccine (antigen), therefore 1 transiently transfected 293 cells successfully expressed fully native human anti-tetanus toxin antibody which specifically recognized tetanus vaccine (antigen).

5. Production and Purification of Fully Native Human Anti-Tetanus Neutralizing Monoclonal Antibody.

Co-transfecting 293 cells with positively identified with neutralizing activity and numbered TRN0010 antibody heavy chain and light chain expression vector (the amino acid sequence of variable region of heavy chain is set forth in SEQ ID NO:7 and the amino acid sequence of variable region of light chain is set forth in SEQ ID NO:8).

Co-transfecting 293 cells with positively identified with neutralizing activity and numbered TRN0012 antibody heavy chain and light chain expression vector (the amino acid sequence of variable region of heavy chain is set forth in SEQ ID NO:17 and the amino acid sequence of variable region of light chain is set forth in SEQ ID NO:18).

Co-transfecting 293 cells with positively identified with neutralizing activity and numbered TRN0010 antibody heavy chain and light chain expression vector (the amino acid sequence of variable region of heavy chain is set forth in SEQ ID NO:22 and the amino acid sequence of variable region of light chain is set forth in SEQ ID NO:26).

Co-transfecting 293 cells with positively identified with neutralizing activity and numbered TRN0010 antibody heavy chain and light chain expression vector (the amino acid sequence of variable region of heavy chain is set forth in SEQ ID NO:22 and the amino acid sequence of variable region of light chain is set forth in SEQ ID NO:26).

Replacing with fresh culture medium 6-8 hours after transfection, and continuously incubating at 37° C. in a 8% CO2 incubator for 96 hours. Collecting transfection supernatant and centrifuging at 4000 rpm for 1 hour, then purifying with Protein A affinity chromatography. Identifying the expression and purity of antibody using SDS-PAGE and Western Blot. As shown in FIGS. 1-4, relatively pure protein was obtained, and the heavy chain and light chain of antibody was clearly identifiable after melting. Note: Lane 1 of FIGS. 1-4A and FIGS. 1-4B representing non-melting protein, Lane 2 of FIGS. 1-4A and FIGS. 1-4B representing protein markers and Lane 3 1 of FIGS. 1-4A and FIGS. 1-4B representing melting protein.

Example 2 Detection of Neutralizing Activities of Neutralizing Monoclonal Antibody Using tetanus vaccine as antigen and coating a 96 well ELISA plate with 10 times diluted antigen, 100 ml per well at 4° C. overnight. Blocking with blocking solutions at room temperature for 2 hours, then incubating with serial dilution of purified antibody as primary antibody at 37° C. for 2 hours, incubating with 1:2000 diluted HRP/anti-His-tag as secondary antibody at 37° C. for 1 h, adding substance color liquid 100 ml per well, placed away from light at room temperature for 5 min, then terminating the reaction with 2M sulfuric acid, and detect at 450 nm wavelength.

Results are shown in FIGS. 5-8. After dilution of purified antibody to not lower than 10,000 times, the concentration of antibody was as low as 0.0002 mg/m l. The diluted antibody still was able to bind to antigen, showing its strong binding activities and neutralizing activities.

Example 3 Measuring Affinity of Neutralizing Monoclonal Antibody

Coupled capturing molecules to CM5 chip and then activating Dextran surface of the chip. The amount of coupling was controlled by sampling time, and lastly capturing ligands with captured molecules. The prepared fully native human anti-tetanus toxin neutralizing monoclonal antibody was used as ligand, and HS-EB buffer diluted tetanus toxin was used as analyte. Analyte with increased concentration passed through the chip orderly, and signals were recorded respectively. Each concentration of analyte reacted with the chip for one cycle and after each cycle, the chip was regenerated with 10 mmol/L glycine-HCl solution to return to its original status with no binding antigen. Kinetic analysis of binding affinity of monoclonal antibody to tetanus toxin was performed using BiaCore X-100 system software.

Results are shown in FIGs. 9-12 and Table 1, the equilibrium dissociation constant of neutralizing monoclonal antibody of this invention to tetanus toxin is lower than $10^{-9}$ mol, indicating it has very high affinity activities.

TABLE 1

Detecting results of affinity of fully native human anti-tetanus toxin neutralizing monoclonal antibody

| Antibody | Ka (l/Ms) | Kd(l/s) | KD(M) |
| --- | --- | --- | --- |
| TRN0010 | 4.15E+04 | 1.53E−04 | 3.68E−09 |
| TRN0012 | 8.06E+04 | 3.28E−04 | 4.07E−09 |
| TRN0011 | 4.27E+04 | 3.87E−05 | 9.05E−09 |
| TRN0015 | 3.88E+04 | 9.40E−05 | 2.43E−09 |

Example 4 Animal Protection Experiments of Anti-Tetanus Toxin Neutralizing Monoclonal Antibody (1) Dilution of Anti-Tetanus Toxin Monoclonal Antibody for Testing The monoclonal antibody was diluted to 100 mg/ml, then a serial of 3 times dilution was made, reserved for testing.

(2) Dilution of Standard Antitoxin

Mixing standard antitoxin saline solution with equal volume neutral glycerin (sterilized at 116° C. for 10 min) then diluting into 0.5 IU/ml solution, that gave IU/10 of every 0.4 ml injection after mixing with equal volume of toxin solution. Each uptake of standard antitoxin solution should not less than 0.5 ml.

(3) Dilution of Toxin

Dissolving freeze-dried powder toxin from Chinese National Biotesting Lab in saline and mixing with equal volume of neutral glycerin (sterilized at 116° for 10 min), then diluting toxin solution with diluent to working concentration.

(4) Determination of Median Lethal Dose (LD50)

Diluting prepared toxin solution to $10^2$, $10^3$, $10^4$, $10^5$, $10^6$, and $10^7$, for at least 2 ml for each dilution level. Taking 0.2 ml and injecting into mice, 4 for each group, and observing for 5 days. Calculating to obtain LD50 using experimental data. The experimental group should use an amount of toxin equal to 20 times or even 60 times of LD50.

(5) Determination of Antibody Titer

To take equal volume of diluted antitoxin and serially diluted antibody into small test tubes, to mix with equal volume of diluted toxin (20 times or 60 times of LD50). After mixing evenly, to seal with test tube plugs, reacting for 1 hour at 37° C. and then to inject immediately in the mice. 140 healthy mice were taken and grouped into 4 mice per group for such experiment. Subcutaneously injecting 0.4 ml above mixtures at abdomen of 18-22 g mice (for negative control groups, injecting 0.2 ml toxin+0.2 ml borate buffered saline; for positive control groups, injecting 0.2 ml toxin+0.2 ml antitoxin; and for experimental groups, injecting 0.2 ml toxin+0.2 ml monoclonal antibody). Observing the status of mice twice every day, one in the morning and one in the afternoon, recording the illness and death of mice.

Results are shown in FIGS. 13-16. When attacked with 20 times LD50 tetanus toxin, all mice in negative control groups were dead, except for the mice in experimental groups with 1.85 mg/ml TRN0010 antibody died after 7 days, all mice in all other experimental groups (0.62 mg/ml, 5.56 mg/ml, 16.67 mg/ml, 50 mg/ml) and all mice in positive control groups survived. This indicate low dose monoclonal antibody as low as 0.62 mg/ml was equivalent to 10 UI/ml standard antitoxin. The monoclonal antibody is able to protect animals from the lethal dose attack of tetanus toxin, and has about the same protective activity as the standard antitoxin. The practical dose of monoclonal antibody of this invention was far lower than that of standard antitoxin, indicating its effects were superior to that of antitoxin. The results indicate that the monoclonal antibody of this invention is capable to neutralize the toxin inside the mice's bodies, to protect the mice and has in vivo activities.

Figure 17:
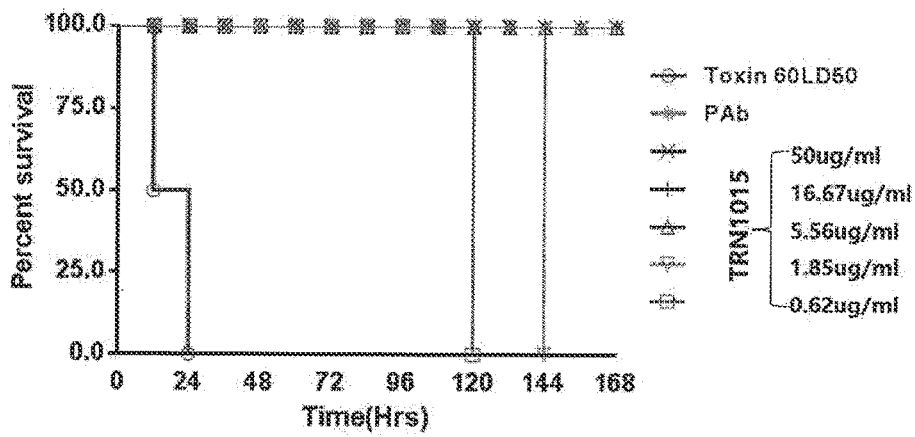
FIG. 17 shows the results for protection effects of TRN0015 antibody against 60 times dose of LD50 tetanus toxin.

As shown in FIG. 17, when under a higher dose tetanus toxin attack (60 times LD50), the mice in negative control groups died within 24 hours, the mice in low dose experimental groups (0.62 mg/ml, 1.85 mg/ml) died within 7 days, the mice in mid and high dose experimental groups (5.56 mg/ml, 16.67 mg/ml and 50 mg/ml) all survived within 7 days, indicating the monoclonal antibody of this invention was able to defend high dose toxin attack, also indicating the monoclonal antibody possesses extremely strong in vivo neutralizing activities.

Though only several examples of specific methods of use are discussed herein above, the technicians of this field should understand that those are just some examples. The scope of protection of this invention is defined in the claims. The technicians of this field may modify or change some of the specific methods of use without deviating from the principle and essence of this invention, all such modifications or changes fall into the scope of protection of this invention.

SEQUENCE LISTING

All the sequences in the specifications and claims are described in a Sequence Listing in a computer readable form (CRF) ASCII text file, which is hereby incorporated by reference of the materials in said Sequence Listing. The name of the ASCII text file is "Trinomab 01_ST25.txt", which is 13,907 bytes in size and created on Sep. 11, 2020.

The invention claimed is:

1. A human neutralizing anti-tetanus toxin monoclonal antibody or an antigen-binding fragment thereof, wherein the antibody or antigen-binding fragment comprises a heavy chain variable domain (VH) having three CDRs and a light chain variable domain (VL) having three CDRs,
wherein the VH comprises an amino acid sequence set forth in any one of SEQ ID NO: 7, SEQ ID NO: 17, SEQ ID NO: 22, or SEQ ID NO: 33, and wherein the VL comprises an amino acid sequence set forth in any one of SEQ ID NO: 8, SEQ ID NO: 18, SEQ ID NO: 26, or SEQ ID NO: 34.

2. The neutralizing monoclonal antibody or the antigen-binding fragment thereof of claim 1, wherein the CDR1, CDR2 and CDR3 of the VH comprise the amino acid sequences set forth in SEQ ID NO: 1, SEQ ID NO: 2 and SEQ ID NO: 3, respectively, wherein the CDR1, CDR2 and CDR3 of the VL comprise the amino acid sequences set forth in SEQ ID NO: 4, SEQ ID NO: 5 and SEQ ID NO: 6, respectively, and wherein the VH comprises the amino acid sequence set forth in SEQ ID NO: 7, and the VL comprises the amino acid sequence set forth in SEQ ID NO: 8.

3. The neutralizing monoclonal antibody or the antigen-binding fragment thereof of claim 1, wherein the CDR1, CDR2 and CDR3 of the VH comprise the amino acid sequences set forth in SEQ ID NO: 9, SEQ ID NO: 10 and SEQ ID NO: 11, respectively, wherein the CDR1, CDR2 and CDR3 of the VL comprise the amino acid sequences set forth in SEQ ID NO: 13, SEQ ID NO: 14 and SEQ ID NO: 15, respectively, and wherein the VH comprises the amino acid sequence set forth in SEQ ID NO: 17, and the VL comprises the amino acid sequence set forth in SEQ ID NO: 18.

4. The neutralizing monoclonal antibody or the antigen-binding fragment thereof of claim 1, wherein the CDR1, CDR2 and CDR3 of the VH comprise the amino acid sequences set forth in SEQ ID NO: 19, SEQ ID NO: 20 and SEQ ID NO: 21, respectively, wherein the CDR1, CDR2 and CDR3 of the VL comprise the amino acid sequences set forth in SEQ ID NO: 23, SEQ ID NO: 24 and SEQ ID NO: 25, respectively, and wherein the VH comprises the amino acid sequence set forth in SEQ ID NO: 22, and the VL comprises the amino acid sequence set forth in SEQ ID NO: 26.

5. The neutralizing monoclonal antibody or the antigen-binding fragment thereof of claim 1, wherein the CDR1, CDR2 and CDR3 of the VH comprise the amino acid sequences set forth in SEQ ID NO: 27, SEQ ID NO: 28 and SEQ ID NO: 29, respectively, wherein the CDR1, CDR2 and CDR3 of the VL comprise the amino acid sequences set forth in SEQ ID NO: 30, SEQ ID NO: 31 and SEQ ID NO: 32, respectively, and wherein the VH comprises the amino acid sequence set forth in SEQ ID NO: 33, and the VL comprises the amino acid sequence set forth in SEQ ID NO: 34.

6. A DNA molecule encoding the neutralizing monoclonal antibody or the antigen-binding fragment thereof of any one of claim 1 or 2-5.

7. A recombinant expression vector, wherein said recombinant expression vector comprises a DNA molecule encoding the neutralizing monoclonal antibody or the antigen-binding fragment thereof of any one of claim 1 or 2-5.

8. A recombinant cell, wherein said recombinant cell is obtained by transformation or transfection of a host cell with a recombinant expression vector comprising a DNA molecule encoding the neutralizing monoclonal antibody or the antigen-binding fragment thereof of any one of claim 1 or 2-5.

9. A complex, wherein said complex comprises the neutralizing monoclonal antibody or the antigen-binding fragment thereof of any one of claim 1 or 2-5 linked covalently to a chemical label or a biological label, wherein said chemical or biological label is selected from an isotope, an immunotoxin, a chemical drug, biotin, avidin, an enzyme, a fluorescent molecule, or an electron transfer agent.

10. A conjugate, wherein said conjugate comprises the neutralizing monoclonal antibody or the antigen-binding fragment thereof of any one of claim 1 or 2-5 conjugated to a solid or semi-solid medium.

11. A composition comprising:
  (a) the neutralizing monoclonal antibody or the antigen-binding fragment thereof of any one of claim 1 or 2-5;
  (b) a complex comprising the neutralizing monoclonal antibody or the antigen-binding fragment thereof of any one of claim 1 or 2-5 linked covalently to a chemical label or a biological label; and/or
  (c) a conjugate comprising the neutralizing monoclonal antibody or the antigen-binding fragment thereof of any one of claim 1 or 2-5 conjugated to a solid or semi-solid medium.

12. A testing product, wherein the testing product comprises:
  (a) the neutralizing monoclonal antibody or the antigen-binding fragment thereof of any one of claim 1 or 2-5;
  (b) a complex comprising the neutralizing monoclonal antibody or the antigen-binding fragment thereof of any one of claim 1 or 2-5 linked covalently to a chemical label or a biological label; and/or
  (c) a conjugate comprising the neutralizing monoclonal antibody or the antigen-binding fragment thereof of any one of claim 1 or 2-5 conjugated to a solid or semi-solid medium;

wherein the testing product comprises a kit, an ELISA plate, or a chip.

13. A method for detecting the presence or the level of tetanus toxin or *Clostridum tetani* in a sample, comprising:
  contacting the sample with the neutralizing monoclonal antibody or the antigen-binding fragment thereof of any one of claim 1 or 2-5, and detecting binding of the antibody or antigen-binding fragment thereof.

14. A method for detecting whether a subject is infected with tetanus toxin or *Clostridum tetani* in a sample, comprising:
  obtaining a sample from the subject;
  contacting the sample with the neutralizing monoclonal antibody or the antigen-binding fragment thereof of any one of claim 1 or 2-5; and
  detecting binding of the antibody or antigen-binding fragment thereof.

15. A method for neutralizing the toxicity of tetanus toxin a sample, comprising:
  contacting the sample with the neutralizing monoclonal antibody or the antigen-binding fragment thereof of any one of claim 1 or 2-5.

* * * * *